United States Patent
Becker et al.

(10) Patent No.: US 7,423,423 B2
(45) Date of Patent: Sep. 9, 2008

(54) METHOD FOR QUANTITATIVELY DETERMINING THE WIDTH OF A SOFT ZONE AREA OF A PARTIALLY HARDENED WORKPIECE

(75) Inventors: Rainer Becker, Ormesheim (DE); Michael Disque, Saarbrucken (DE); Andre Yashan, Saarbrucken (DE)

(73) Assignee: Fraunhofer-Gesellschaft zur Forderung der angewandten Forschung e.V., München (DE)

( * ) Notice: Subject to any disclaimer, the term of this patent is extended or adjusted under 35 U.S.C. 154(b) by 0 days.

(21) Appl. No.: 10/578,724

(22) PCT Filed: Sep. 15, 2004

(86) PCT No.: PCT/EP2004/010287

§ 371 (c)(1),
(2), (4) Date: May 14, 2007

(87) PCT Pub. No.: WO2005/052568

PCT Pub. Date: Jun. 9, 2005

(65) Prior Publication Data

US 2007/0273355 A1    Nov. 29, 2007

(30) Foreign Application Priority Data

Nov. 10, 2003  (DE) ................. 103 52 422

(51) Int. Cl.
*G01N 27/72* (2006.01)
*G01R 33/12* (2006.01)
*G01R 35/00* (2006.01)

(52) U.S. Cl. ................. 324/232; 324/228; 324/202

(58) Field of Classification Search ................. 324/232, 324/71.1, 240, 228, 233, 234, 236, 237, 239, 324/241, 242, 243, 202, 207.15, 224; 73/761, 73/866.1; 219/665, 663, 667, 608, 670; 148/567; 266/129
See application file for complete search history.

(56) References Cited

U.S. PATENT DOCUMENTS 6,287,009 B1 * 9/2001 Nakamura et al. ........... 384/448
6,576,877 B2 * 6/2003 Dabelstein et al. .......... 219/640

FOREIGN PATENT DOCUMENTS

DE    36 20 491 C2    12/1987
DE    43 10 894 A1    10/1994

* cited by examiner

*Primary Examiner*—Reena Aurora
(74) *Attorney, Agent, or Firm*—Antonelli, Terry, Stout & Kraus, LLP.

(57) ABSTRACT

Disclosed is a method for quantitatively determining the width of a soft zone area of a partially hardened metallic workpiece, which has at least one hardened and one unhardened area, by means of at least one multifrequency eddy current sensor. A single workpiece being individually is moved relative to the multifrequency eddy current sensor in such a manner that a spatially delimited eddy current field generated by the multifrequency eddy current interacts with the workpiece contactlessly, generates eddy currents therein which, in turn, generate a measuring signal in the multifrequency eddy current sensor, in which the spatially delimited eddy current field has a greatest extension oriented in longitudinal direction to the surface of the workpiece which extension is greater than the maximum extension of the soft zone area in longitudinal direction of the surface of the workpiece.

26 Claims, 2 Drawing Sheets

METHOD FOR QUANTITATIVELY DETERMINING THE WIDTH OF A SOFT ZONE AREA OF A PARTIALLY HARDENED WORKPIECE

BACKGROUND OF THE INVENTION

1. Field of the Invention

The present invention relates to a method for quantitatively determining the width of a soft zone area of a partially hardened metallic workpiece having at least one hardened and one unhardened area by means of at least one multifrequency eddy current sensor.

2. Description of the Prior Art

Components that often are used in automatic transmissions are so-called planetary transmissions, whose gear teeth continuously intermesh. Despite the multiplicity of differently designed planetary transmissions, all these types of transmissions have in common that at least one gear which is designed as a planet wheel intermeshes with a centrally placed sun wheel and a peripherally running ring gear wheel. Usually so-called planet wheel bolts run through the center of the planet wheels, extending on both sides. In order to produce such type planet wheel bolts, solid or hollow cylindrical metallic rods are cut to the desired length. In order to improve the solidity of the material, the cut cylindrical pieces are subjected to a hardening process. For subsequent processing of the front ends of the individual cylindrical workpieces, the respective front ends are not subjected to the hardening process. It is known to harden the workpiece with induction hardening which effectively heats practically the entire cylindrical workpiece with the exception of the areas at the front ends of the workpiece. The front end areas of the workpiece that should not intentionally be subjected to the hardening process have, depending on the respective size of the workpiece, an axial extension, having a width, of a few millimeters, which preferably is between 1.5 mm and 2.5 mm.

The front ends of cylindrical workpieces which are partially hardened in the aforedescribed manner are then processed usually by means of a material-removing process. It is easy to understand that if the workpiece were fully hardened it would be much more difficult to carry out the finishing step and would subject the removal tool to much more wear. For this reason, there is particular interest in partially hardening, cylindrical workpieces which are half-finished products in order to ensure that the front ends of the partially hardened workpieces represent unhardened so-called "soft zone areas".

Previously, in order to control the quality of the partially hardened half-finished products known control methods were used, such as, for example, visual inspection of the front soft zone areas which requires an educated inspection in order to be able to distinguish the hardened area of the workpiece from the unhardened one. At a suitable angle of vision and under suitable lighting conditions, light reflects in a minimally different manner. This light scattering is on the surface of the soft zone area rather than on the surface region of the hardened workpiece. This control method is expensive and time consuming. Moreover the inspection staff is prone to become tired resulting in reliability not being ensured in the desired manner.

In order to avoid employing staff, there is one known optical control measuring method known which permits detecting the color differences resulting from the light scattering of the soft zone area differing from the hardened zone.

In addition to optical methods, electro-magnetic methods are known, for example, the multifrequency eddy current method described, for example in DE 36 20 491 C2. The eddy current principle detects surface flaws as well as differences in the microstructure from irregularities in the induced eddy currents. Scanning probes or encircling probes induce these eddy currents and simultaneously measure the electro-magnetic fields generated by these eddy currents. Evaluation of the measuring signals obtained by means of the multifrequency eddy current method described in the preceding printed publication is based on elliptical evaluation in the impedance plane using a multiplicity of measuring frequencies which permits a solely qualitative finding of the to-be-examined workpiece. With the previous evaluation methods, it is not possible to state the absolute size of the soft zone areas.

Also known are so-called magnetic Barkhausen noise methods with which high-frequency Barkhausen oscillations are induced in the workpiece under examination by means of dynamic reverse magnetization processes. The high-frequency Barkhausen oscillation can be detected by a magnet-inductive receiver. The intensity of the Barkhausen noise is much more intense in the soft zone area than in the hardened zone area so that it is possible to discern and measure the differences in the two workpiece areas. A disadvantage, however, is the necessity of an excitation yoke and the great sensitivity to disturbing outside influences, which permits industrial use to only a limited extent.

DE 43 10 894 A1 describes a method and a testing probe for non-destructive examination of surfaces of electrically conductive workpieces. The disclosed testing probe should enable obtaining information about the hardness, thickness and state of the microstructure of an electrically conductive workpiece. An interaction occurs between the magnetic alternating field acting in the workpiece and the measurable voltage induced in the testing coil of the multifrequency alternating field sensor. With the aid of a multifrequency eddy current sensor, information can be gained about at least one material property of the surface under examination in the area of the penetration depth of the magnetic alternating field. In particular, the prior art method for determining the course of a hardness profile along an electrically conductive workpiece being examined serves to determine the thickness of the respective surface layers on the workpiece.

SUMMARY OF THE INVENTION

The present invention provides a method for determining quantitatively the size of a soft zone area of a partially hardened metallic workpiece, which has at least one hardened and one unhardened area, using at least one multifrequency eddy current sensor, in such a manner permitting quick and exact quantitative determination of the soft zone area of a partially hardened workpiece, which is preferably a planet wheel bolt present in a form of a half finished product, by means of simple and cost-effective means. It should be possible to use the method on an industrial scale and in inline operation, that is on a continuously or pulsed operated production line.

The quantitative measurement with which the soft zone area should be measured should be sufficiently exact to have for example a precision of ±0.3 mm.

According to the method of the invention, a workpiece is moved relative to a multifrequency current eddy sensor in such a manner that an eddy current field generated by the multifrequency eddy current sensor interacts contactlessly with the workpiece in a spatially limited manner. Eddy currents are generated in the workpiece which, in turn, generate a measuring signal in the multifrequency eddy current sensor. The limited eddy current field has a greatest extension and extends farthest in a longitudinal direction of the surface of the workpiece. The extension of the eddy current field is greater than a maximum extension of the soft zone area in the longitudinal direction of the surface of the workpiece.

With the aforementioned measuring preconditions, in a first step calibrated data obtained from a number n of workpieces n is generated which preferably are from the group of the workpieces to be measured. A predetermined standard size of the width of the soft zone is assumed which is the desired size of an extension oriented in longitudinal direction along the surface of the workpiece. The measuring signals of the n workpieces are used to plot a calibration curve. Then the calibration curve obtained in this manner, is used subsequently on the n workpieces which are measured in the same manner. Based on the calibration curve, the measuring signals which are obtained can now each be assigned to absolute soft zone widths.

The method of the invention is therefore distinguished by, in a first step, by a dynamic calibration which correlates the measuring signals with desired sizes of actual soft zone widths as absolute values, occurring while the workpieces are being conveyed to the measuring sensor in a continuously pulsed manner. In a second step, the soft zone widths of all the workpieces which are subsequently conveyed to the multifrequency measuring sensor are then quantitatively determined with high precision. The method of the invention, thus, can be used on industrial production lines without slowing the flow of the workpieces on the conveyer belt since the quality control step is completely contactless.

The method of the invention is described in the following with reference to measuring planet wheel bolts as half-finished products, which as mentioned in the preceding have a cylindrical shape and two soft zone areas provided on their front ends. The front end soft zone areas are separated from each other by a hardened middle area which is longer in the axial direction.

Of course, the method of the invention can also be applied to alternative partially hardened workpieces where information about an exact spatial extension either hardened or unhardened workpiece areas is required.

BRIEF DESCRIPTION OF THE DRAWINGS

The present invention is made more apparent by way of example in the following without the intention of limiting the overall inventive idea using preferred embodiments with reference to the accompanying drawings.

DESCRIPTION OF THE INVENTION

Figure 1:
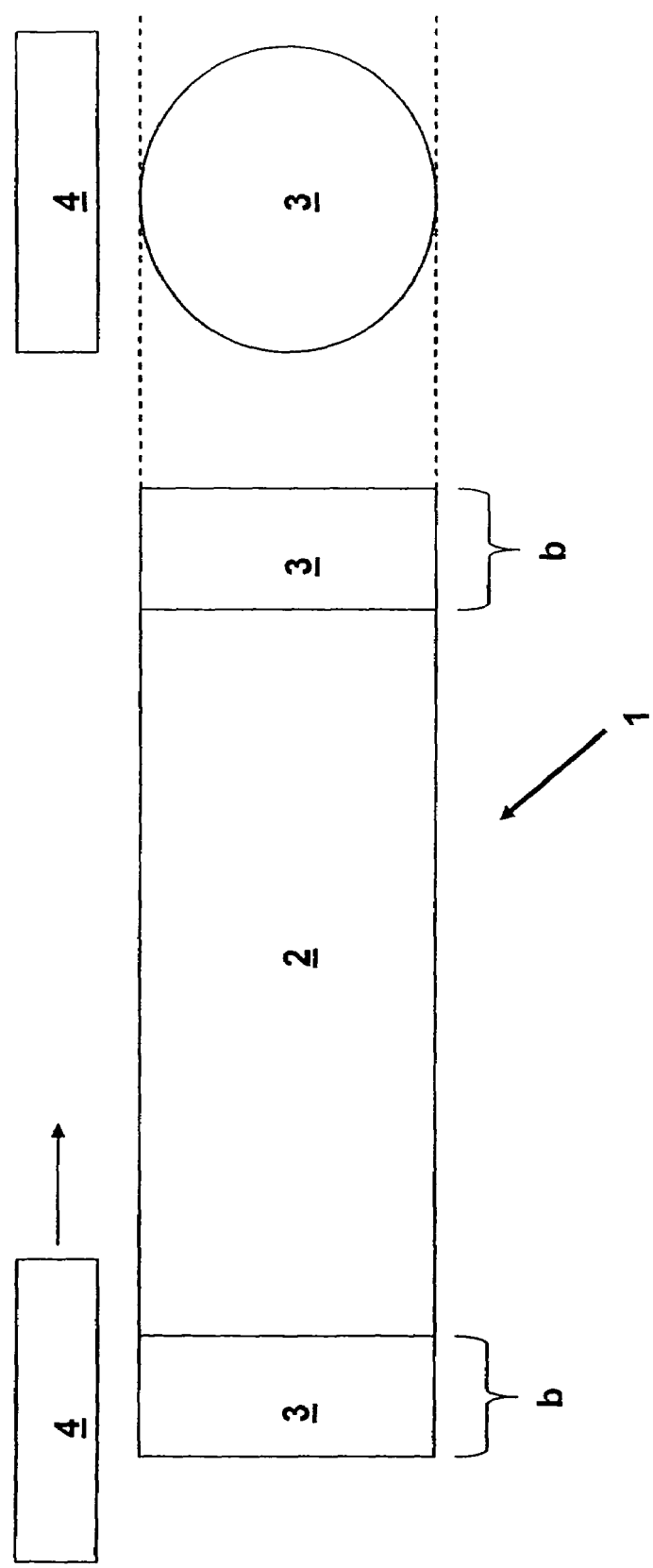
FIG. 1 shows a schematic representation of a partially hardened planet wheel bolt with a multifrequency eddy current sensor.

FIG. 1 shows very schematically a planet wheel bolt 1 which usually is made of a solid metallic material and has, by means of induction hardening, a hardened zone 2 in the middle region of the bolt 1. FIG. 1 shows both a lateral as well as a front view of the measuring situation. Adjacent to the hardened zone 2 on both sides are unhardened areas 3. These so-called soft zone areas 3 terminate at the front ends of the planet wheel bolt 1. Depending on the shape and dimensions of the planet wheel bolt 1, the soft zone areas 3 usually have an axial longitudinal extension. A soft zone width b ranges between 1.5 mm and 2.5 mm.

Exact measurement of the soft zone width b, is important for subsequent processes. The planet wheel is a half-finished product with an outer shape, which for example is determined by selective material removal inside the soft zone area 3. The multifrequency eddy current sensor 4 is moved parallel to the longitudinal extension of the planet wheel bolt 1 along a distance in the direction depicted in FIG. 1. In an industrial application, it is advantageous if the multifrequency eddy current sensor 4 rests in place and the workpieces which are measured are conveyed one at a time to the sensor area along a conveyor path.

The multifrequency eddy current sensor 4 possesses an effective width which is oriented in the direction of movement (see arrow). The effective width is larger than the axial extension of the soft zone width 3 so that it is ensured that with suitable positioning relative to the planet wheel bolt 2, the eddy current field generated by the multifrequency eddy current sensor 4 extends completely over the soft zone area 3.

For exact determination of the soft zone width b, a measurement constellation has to be created in which the multifrequency eddy current sensor 4 extends completely over the soft zone 3, with the eddy current field generated by the multifrequency eddy current sensor 4 simultaneously being able to penetrate a partial area of the hardened zone adjacent to the soft zone 3. FIG. 1 shows such a measurement.

As the relative movement between the multifrequency eddy current sensor 4 and the planet wheel bolt 1 occurs with a constant velocity, the time point, for the measurement as shown in FIG. 1, has to be determined in which the sought measurement of the sought soft zone width b is possible.

Usually, detection of the measuring signals by means of the multifrequency eddy current sensor 4 occurs in a pulsed manner so that a multiplicity of single measuring signals are detected while the eddy current measuring sensor 4 moves over the entire length of the planet wheel bolt 1. The multifrequency eddy current sensor 4 is operated in an advantageous manner with 4 different test frequencies so that ultimately 4 measuring signals are obtained per measuring point. For further evaluation with a complex impedance level, the measuring signals are each split into real and imaginary parts according to phase and amplitude. Thus there are 8 different measuring signal components available for signal evaluation per measuring point.

Figure 2:
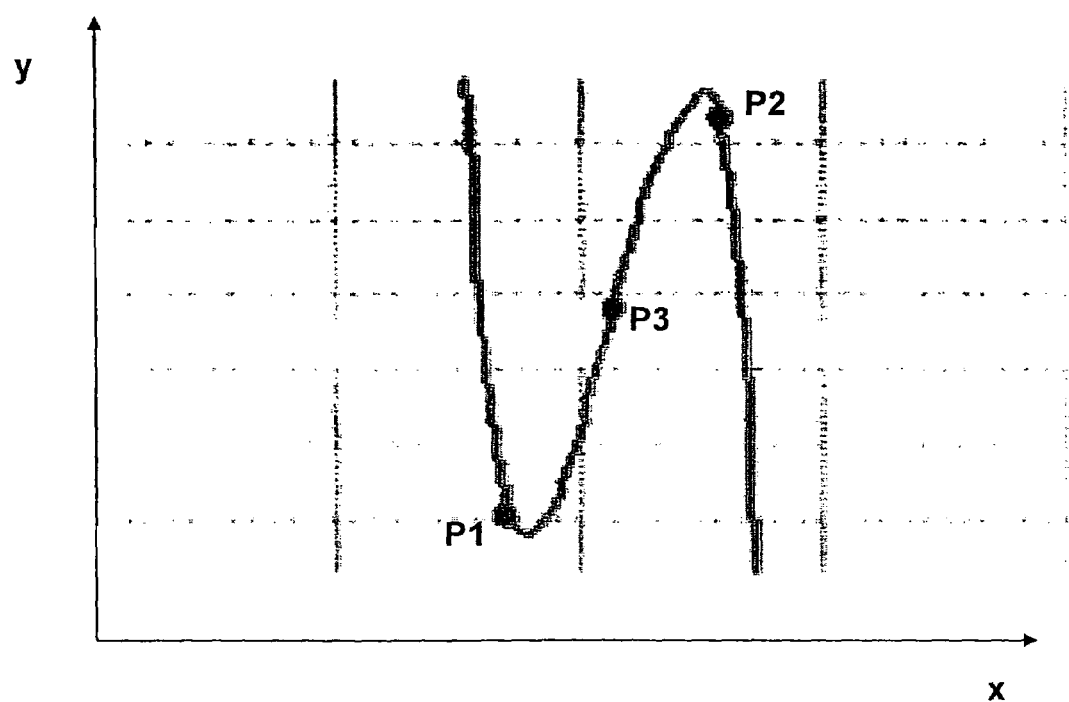
FIG. 2 shows a qualitative, diagrammatic representation of an amplitude locus curve for determining a defined relative position between the workpiece which is to be measured and the multifrequency sensor.

From the measuring signals which are obtained during the relative movement of the multifrequency eddy current sensor 4 along the surface in the axial direction to the planet wheel bolt 1, the measuring signals can be represented in the form of an amplitude locus curve for each measuring frequency. The amplitude locus curve (X-axis corresponding to the locus coordinate and the amplitude levels of the measuring signal are plotted along the Y-axis) shown in FIG. 2 permits exact extraction of the measuring signal obtained in the aforedescribed measuring required for measuring the soft zone width b. The determination, and selection, of the measuring signal required for measurement evaluation from the amplitude locus curve occurs based on empirically obtained data if the relative velocity between the sensor and the workpiece is sufficiently constant.

In the same manner that the measuring signal is extracted for determining the width of the soft zone shown in FIG. 1 as the left soft zone 3, a measuring signal for determining the width of the right soft zone 3 of FIG. 1 can also be derived.

The preceding description shows that the relative spatial position between the multifrequency eddy current sensor 4 and the planet wheel bolt 1 which is to be measured can be determined contactlessly solely using the measuring signals obtained with the multifrequency eddy current sensor 4.

Before the measuring signals which are obtained, which are present as amplitude and phase data, can be assigned to exact width values b (for example by giving absolute mm values), the measuring signals must be calibrated. Calibration according to the present invention, is carried out dynamically, that is during normal production conveyance of the planet wheel bolts to be measured to the multifrequency eddy current sensor 4. Provided that the partially hardened planet wheel bolts, which are present as half-finished products (so-called "Okay parts"), that is planet wheel bolts with known correctly dimensioned soft zone widths b, the first number n of the workpieces conveyed to the multifrequency eddy current sensor 4 are selected for calibration. Single planet wheel bolts are measured for calibration purposes in a suitable manner, with the planet wheel bolts measured in the afore-described manner always yielding the measuring signals which are correlated with absolute soft zones widths b. In order to, for example, extract the measuring signal which represents the soft zone width b adjacent to the left front end of the planet wheel bolt 1 from the amplitude locus curve, the point P1 is selected based on the empirically gained data. The number of the measuring signals lying between the point P1 and the minimum is determined empirically. Selection of the point P2 which represents the width of the right soft zone occurs in the same manner.

However, determining a calibration curve requires, at least one additional measuring point yielded by detecting a measuring signal in the center of the planet wheel bolt, which is the center of the hardened zone 2. The measuring signal P3 is located between the minimum and the maximum of the amplitude locus curve. As it can be assumed with certainty that this region contains no soft areas, the soft zone width b equals zero. Based on these two measuring values, a calibration curve is plotted, which is used as a basis for further measurement of the subsequent planet wheel bolts.

All the planet wheel bolts following in the conveyance direction of the planet wheel bolts which have already been measured for calibration purposes, are measured with regard to their soft zone widths b in the identical manner. However, this measurement is on the basis of the obtained calibration curve. This is done by assigning the measuring signals obtained on the defined measurements to the width values relative to the soft zone 3 which can be obtained from the calibration curve.

In order to further increase measurement precision, the planet wheel bolts used for calibration purposes can subsequently be measured regarding their respective soft zone widths b using conventional measuring methods. If the conventional measuring methods, for example visual measurement of the soft zone width of etched bolts, in which the soft zone differs distinctly in color from the hardened zone, deviate from the measuring signal obtained by means of the dynamic calibration, the calibrated curve can be corrected accordingly.

With the method of the invention, planet wheel bolts can be conveyed along a conveyance path to a multifrequency eddy current sensor in such a manner that it is possible to measure precisely up to 60 planet wheel bolts a minute. The measurements can be conducted with a quantitative precision of ±0.3 mm regarding the width value of the soft zone. This extraordinarily high precision and reliability of the testing method results in a very low pseudo-reject rate.

LIST OF REFERENCES

1 planet wheel bolt
2 hardened zone
3 soft zone
4 multifrequency eddy current sensor

What is claimed is:

1. A method for quantitatively determining a width of a soft zone area of a partially hardened metallic workpiece, which has at least one hardened and one unhardened area, with at least one multifrequency eddy current sensor, wherein:

a single workpiece is individually moved relative to the multifrequency eddy current sensor so that a spatially limited eddy current field generated by the multifrequency eddy current interacts with the workpiece contactlessly, generates eddy currents therein which generate a measuring signal in the multifrequency eddy current sensor, in which the spatially limited eddy current field has a greatest extension along a longitudinal direction of a surface of the workpiece, the greatest extension of the eddy current field being greater than a maximum extension of the soft zone area along the longitudinal direction of the surface of the workpiece; and measuring a number n of workpieces for calibrating purposes, using the measuring signals of the n workpieces to plot a calibration curve using a predetermined standard size of a width of the soft zone with a desired size of an extension oriented in a longitudinal direction of the soft zone area of the n workpieces, and assigning an absolute soft zone width to the measuring signals based on the calibration and which are obtained from each individual workpiece.

2. The method according to claim 1, wherein:
the workpieces are cylindrical and are moved relative to the eddy current sensor along a cylindrical axis thereof.

3. The method according to claim 2 wherein:
the multifrequency eddy current sensor is operated so that during measuring of a workpiece, which moves continuously relative to the multifrequency sensor with a constant velocity, a multiplicity of the measuring signals are generated and plotted as an amplitude locus curve; and from at least one part of the amplitude locus curve a measuring constellation is selected in which the workpiece has a defined position to the multifrequency eddy current sensor, in which defined position a measuring signal is recorded which is used to determine a width of the soft zone.

4. The method according to claim 3, wherein:
the defined position is selected so that the eddy current field of the multifrequency eddy current sensor completely contains the soft zone area at least in a longitudinal extension relative to a longitudinal direction of movement.

5. The method according to claim 4, wherein:
the defined position is determined solely by evaluation of the amplitude locus curve.

6. The method according to claim 5, wherein:
a multifrequency eddy current sensor with four different testing frequencies is used as the multifrequency eddy current sensor.

7. The method according to claim 4, wherein:
a multifrequency eddy current sensor with four different testing frequencies is used as the multifrequency eddy current sensor.

8. The method according to claim 3, wherein:
a multifrequency eddy current sensor with four different testing frequencies is used as the multifrequency eddy current sensor.

9. The method according to claim 2, wherein:
a multifrequency eddy current sensor with four different testing frequencies is used as the multifrequency eddy current sensor.

10. The method according to claim 1, wherein:
the workpieces are planet wheel bolts which have a cylindrical geometry and two soft areas located on ends thereof separated by a hardened middle area, with the middle area having a greater axial extension than the soft zone areas, which each have an axial extension, and a soft zone width, from 1.5 mm to 2.5 mm.

11. The method according to claim 10 wherein:
the multifrequency eddy current sensor is operated so that during measuring of a workpiece, which moves continuously relative to the multifrequency sensor with a constant velocity, a multiplicity of the measuring signals are generated and plotted as an amplitude locus curve; and
from at least one part of the amplitude locus curve a measuring constellation is selected in which the workpiece has a defined position to the multifrequency eddy current sensor, in which defined position a measuring signal is recorded which is used to determine a width of the soft zone.

12. The method according to claim 10, wherein:
a multifrequency eddy current sensor with four different testing frequencies is used as the multifrequency eddy current sensor.

13. The method according to claim 11, wherein:
the defined position is selected so that the eddy current field of the multifrequency eddy current sensor completely contains the soft zone area at least in a longitudinal extension relative to a longitudinal direction of movement.

14. The method according to claim 13, wherein:
the defined position is determined solely by evaluation of the amplitude locus curve.

15. The method according to claim 14, wherein:
a multifrequency eddy current sensor with four different testing frequencies is used as the multifrequency eddy current sensor.

16. The method according to claim 11, wherein:
a multifrequency eddy current sensor with four different testing frequencies is used as the multifrequency eddy current sensor.

17. The method according to claim 13, wherein:
a multifrequency eddy current sensor with four different testing frequencies is used as the multifrequency eddy current sensor.

18. The method according to, claim 1 wherein:
the multifrequency eddy current sensor is operated so that during measuring of a workpiece, which moves continuously relative to the multifrequency sensor with a constant velocity, a multiplicity of measuring signals is generated and plotted as an amplitude locus curve; and
from at least one part of the amplitude locus curve a measuring constellation is selected in which the workpiece has a defined position to the multifrequency eddy current sensor, in which defined position a measuring signal is recorded which is used to determine a width of the soft zone.

19. The method according to claim 18, wherein:
the defined position is selected so that the eddy current field of the multifrequency eddy current sensor completely contains the soft zone area at least in longitudinal extension to a direction of movement.

20. The method according to claim 19, wherein:
a multifrequency eddy current sensor with four different testing frequencies is used as the multifrequency eddy current sensor.

21. The method according to claim 18, wherein:
the defined position is determined solely by evaluation of the amplitude locus curve.

22. The method according to claim 21, wherein:
a multifrequency eddy current sensor with four different testing frequencies is used as the multifrequency eddy current sensor.

23. The method according to claim 18, wherein:
a multifrequency eddy current sensor with four different testing frequencies is used as the multifrequency eddy current sensor.

24. The method according to claim 1, wherein:
a multifrequency eddy current sensor with four different testing frequencies is used as the multifrequency eddy current sensor.

25. The method according to claim 1, wherein:
the workpieces are planet wheel bolts which have a cylindrical geometry and two soft areas located on ends thereof separated by a hardened middle area, with the middle area having a greater axial extension than the soft zone areas, which each have an axial extension and a soft zone width from 1.5 mm to 2.5 mm.

26. The method according to claim 25, wherein:
a multifrequency eddy current sensor with four different testing frequencies is used as the multifrequency eddy current sensor.

* * * * *